(12) United States Patent
Wang et al.

(10) Patent No.: US 9,156,777 B2
(45) Date of Patent: Oct. 13, 2015

(54) PROCESS FOR PREPARING N-ACYL AMINO ACID SALTS

(71) Applicant: Stepan Company, Northfield, IL (US)

(72) Inventors: Bing Wang, Niles, IL (US); Gregory P Dado, Chicago, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 14/411,971

(22) PCT Filed: Jun. 27, 2013

(86) PCT No.: PCT/US2013/048341
§ 371 (c)(1),
(2) Date: Dec. 30, 2014

(87) PCT Pub. No.: WO2014/008103
PCT Pub. Date: Jan. 9, 2014

(65) Prior Publication Data
US 2015/0126776 A1    May 7, 2015

Related U.S. Application Data

(60) Provisional application No. 61/667,568, filed on Jul. 3, 2012.

(51) Int. Cl.
*C07C 233/91* (2006.01)
*C07C 231/02* (2006.01)
*C07C 231/10* (2006.01)

(52) U.S. Cl.
CPC ............. *C07C 233/91* (2013.01); *C07C 231/02* (2013.01); *C07C 231/10* (2013.01)

(58) Field of Classification Search
CPC .......................... C07C 233/91; C07C 231/10
See application file for complete search history.

(56) References Cited

U.S. PATENT DOCUMENTS

| | | | |
|---|---|---|---|
| 3,836,551 A | 9/1974 | Schroeder et al. | |
| 4,380,646 A | 4/1983 | Franzmann | |
| 5,856,538 A | 1/1999 | Strecker et al. | |
| 5,898,084 A | 4/1999 | Oftring et al. | |
| 6,703,517 B2 | 3/2004 | Hattori et al. | |
| 6,828,452 B2 | 12/2004 | Raths et al. | |
| 8,093,414 B2 | 1/2012 | Klug et al. | |
| 2004/0063980 A1* | 4/2004 | Raths et al. ................ 554/69 |
| 2006/0239952 A1* | 10/2006 | Hattori ................ 424/70.14 |
| 2009/0062177 A1 | 3/2009 | Tsaur | |
| 2009/0156450 A1 | 6/2009 | Tsaur | |
| 2010/0075881 A1 | 3/2010 | Tsaur | |
| 2010/0273879 A1 | 10/2010 | Klug et al. | |
| 2010/0305358 A1 | 12/2010 | Klug et al. | |
| 2011/0245125 A1 | 10/2011 | Tsaur et al. | |
| 2013/0029899 A1 | 1/2013 | Hermanson et al. | |
| 2013/0030197 A1 | 1/2013 | Harichian et al. | |
| 2013/0030198 A1 | 1/2013 | Harichian et al. | |
| 2013/0030199 A1 | 1/2013 | Harichian et al. | |
| 2013/0030200 A1 | 1/2013 | Harichian et al. | |
| 2013/0030201 A1 | 1/2013 | Harichian et al. | |
| 2013/0030202 A1 | 1/2013 | Harichian et al. | |
| 2013/0030203 A1 | 1/2013 | Harichian et al. | |

FOREIGN PATENT DOCUMENTS

| | | |
|---|---|---|
| DE | 4408957 | 9/1995 |
| EP | 1672055 | 6/2006 |
| WO | 9507881 | 3/1995 |
| WO | 2013014268 | 1/2013 |
| WO | WO 2013014268 A1 * | 1/2013 |

OTHER PUBLICATIONS

E. Jungermann et al., J. Am. Chem. Soc. 78 (1956) 172.
K. Kochetkov et al., Bull. Acad. Sci. USSR 39 (1990) 2311.
PCT Search Report mailed in PCT/US2013/048341 on Oct. 2, 2013.
PCT Search Report mailed in PCT/US2014/050219 on Nov. 17, 2014.

* cited by examiner

*Primary Examiner* — Sudhakar Katakam
(74) *Attorney, Agent, or Firm* — Dilworth IP LLC

(57) ABSTRACT

Improved processes for making an N-acyl amino acid salt from a fatty alkyl ester or a polyol ester are disclosed. Each process uses a polyol selected from glycerin or propylene glycol in an amount effective to keep the reaction mixture fluid until conversion to the N-acyl amino acid salt reaches the desired level of completion. In one process, a fatty alkyl ester reacts with an amino acid salt in the presence of glycerin or propylene glycol to produce an N-acyl amino acid salt. In another process, a polyol ester reacts with the amino acid salt in the presence of added glycerin or propylene glycol to produce the N-acyl amino acid salt. We surprisingly found that an effective amount of glycerin or propylene glycol minimizes or eliminates reaction mixture solidification or foaming, reduces color, and minimizes the level of di- and tripeptide by-products. In a related process, water is added when conversion of the amino acid salt to the N-acyl amino acid salt is in the range of 50 to 90 mole %. Water addition improves processability, advances conversion without producing excessive soap, and helps to ensure that the N-acyl amino acid salt will have low color and a small proportion of by-products.

26 Claims, No Drawings

US 9,156,777 B2

PROCESS FOR PREPARING N-ACYL AMINO ACID SALTS

FIELD OF THE INVENTION

The invention relates to N-acyl amino acid salts and processes for preparing them.

BACKGROUND OF THE INVENTION

N-Acyl amino acid salts are anionic surfactants useful in laundry detergents, household or industrial cleaners, foamers, emulsifiers, personal cleansers, and other applications. Because they are often exceptionally mild, the salts are particularly valuable for personal care formulations.

In general, N-acyl amino acid salts have been underutilized, due at least in part to challenges in manufacturing them. N-Acyl amino acid salts can be made from the corresponding fatty acyl chlorides and amino acid salts using Schotten-Baumann chemistry (see, e.g., J. Am. Chem. Soc. 78 (1956) 172 and U.S. Pat. No. 6,703,517), but this process is expensive and generates an equimolar amount of undesirable salt by-product. In an alternative synthetic method, a fatty acid is reacted with an amino alcohol to give a fatty amide, which is then oxidized to give the N-acyl amino acid (see, e.g., U.S. Pat. No. 8,093,414). This process is hampered by relatively low yields, low selectivities in the oxidation step, the use of precious metal catalysts, and the need for a conventional organic workup.

In other known processes, the N-acyl amino acid salt is made from a fatty acid. For example, EP 1672055 and U.S. Pat. Appl. Publ. No. 2006/0239952 describe the synthesis of N-acyl glycinates by reacting a fatty acid with glycine. This process generates a relatively high proportion of di- and tripeptide by-products (di- and triglycinates), which may or may not be desirable depending upon the intended use; conversion to the mono-acylated product is about 92%. U.S. Pat. No. 3,836,551 teaches to react fatty acids with amino acid salts either in the molten fluid phase (i.e., without a solvent), in solution using a polar aprotic solvent (such as dimethyl sulfoxide or N,N-dimethylformamide), or in suspension with a nonpolar organic solvent (e.g., xylene). Typical reaction times are about 9 hours, and by-products are not discussed. Generally, the fatty acid route is also less preferred because it requires a high reaction temperature, which leads to undesirable color development in the N-acyl amino acid salt.

Fatty esters have also been used as starting materials. U.S. Pat. No. 5,856,538 teaches to react a fatty alkyl ester (e.g., methyl oleate) with an amino acid salt and a 30-150% molar excess of a strong base (e.g., sodium methoxide/methanol solution). Sodium sarcosinate is used in the examples, although other amino acid salts are taught as suitable, and no solvent is used. WO 95/07881 teaches a method of preparing N-acyl sarcosinates starting from fatty esters. The reference indicates that alcohol solvents (e.g., 1-propanol, 1-butanol, isobutyl alcohol, propylene glycol, ethylene glycol) can be used to reduce viscosity during the amidation reaction. In the examples, the solvent is used to remove water by azeotropic distillation.

U.S. Pat. No. 5,898,084 describes the preparation of N-acyl amino acid salts by reacting a mono-, di-, or triglyceride with an amino acid salt in the presence of a strong base. In the examples, colza oil (a triglyceride) is reacted with sodium sarcosinate in the presence of sodium methoxide/methanol, and the reaction continues until glycerides are no longer detected. A typical organic workup follows. The reference indicates that the glycerin produced in the course of the reaction either remains in the reaction mixture or is partly or wholly removed in the conventional workup. At the conclusion of the reaction, the mixture is typically a viscous paste.

The preparation of N-acyl amino acid salts is particularly challenging when the reactants are fatty alkyl esters—particularly fatty methyl esters—and alkali metal glycinates, as in the preparation of sodium cocoyl glycinate, sodium myristyl glycinate, or sodium lauryl glycinate. This reaction is troublesome due to a lack of reagent compatibility, solidification of the reaction mixture at elevated process temperatures, color development, severe foaming during methanol removal, and significant by-product generation. Solvents have been used to mitigate some of these concerns but typically in the context of sarcosinates or other amino acid salts that are more easily converted to N-acyl amino acid salts. Moreover, the need to remove a solvent introduces additional challenges.

In sum, an improved process for making N-acyl amino acid salts is needed. In particular, the industry needs a process that avoids salt generation and the selectivity issues of other known routes. Preferably, the process would give a reduced proportion of di- and tripeptide by-products and would avoid the need to remove a process solvent. An ideal process would overcome the particular difficulties that complicate the preparation of N-acyl glycinates from fatty alkyl esters.

SUMMARY OF THE INVENTION

The invention relates to improved processes for making an N-acyl amino acid salt from a fatty alkyl ester or a polyol ester. Each process uses at least one polyol selected from glycerin and propylene glycol in an amount effective to keep the reaction mixture fluid until conversion to the N-acyl amino acid salt reaches the desired level of completion.

One process comprises reacting a fatty alkyl ester with an amino acid salt in the presence of glycerin or propylene glycol to produce an N-acyl amino acid salt and a $C_1$-$C_4$ alkanol. The alkanol is removed from the reaction mixture as it forms. Another process comprises reacting a polyol ester selected from mono-, di- or triglycerides or fatty mono- or diesters of propylene glycol with the amino acid salt in the presence of added glycerin or propylene glycol to produce the N-acyl amino acid salt.

We surprisingly found that an effective amount of glycerin or propylene glycol in the process minimizes or eliminates reaction mixture solidification or foaming at the reaction temperature, reduces color, and minimizes the level of di- and tripeptide by-products. Because the propylene glycol or glycerin can be left in the reaction product for some end uses, particularly personal care applications, the process obviates the need to remove and recover a process solvent.

In a related process, water is added to the reaction mixture when conversion of the amino acid salt to the N-acyl amino acid salt is in the range of 50 to 90 mole %. Water addition improves processability, unexpectedly advances conversion without producing excessive soap, and helps to ensure that the N-acyl amino acid salt will have low color and a small proportion of di- and tripeptide by-products.

DETAILED DESCRIPTION OF THE INVENTION

Preparation of N-Acyl Amino Acid Salts from Fatty Alkyl Esters

One process comprises reacting a fatty alkyl ester with an amino acid salt in the presence of a polyol selected from glycerin and propylene glycol to produce an N-acyl amino acid salt and a $C_1$-$C_4$ alkanol.

Suitable fatty alkyl esters are lower alkyl esters of linear or branched, saturated or unsaturated fatty acids. The fatty alkyl ester can be made, for example, by esterifying a fatty acid with an alkanol or by transesterifying a triglyceride, which is typically an animal or vegetable fat or oil, with an alkanol. Consequently, the fatty portion of the ester will typically have 6-22 carbons with a mixture of saturated and internally unsaturated chains.

In a preferred aspect, the fatty alkyl ester is a lower alkyl ester obtained by fractionation. Thus, saponification of a fat or oil provides a fatty acid, which can be reacted with a lower alkanol to give a mixture of esters, typically methyl esters. Fractionation of this mixture provides fatty alkyl esters having a desired average carbon number range. Alternatively, the fat or oil is transesterified with an alkanol to give the esters in one step prior to fractionation.

Depending on the source, the fatty ester may have a preponderance of $C_{16}$-$C_{22}$ component. For instance, methanolysis of soybean oil provides the saturated methyl esters of palmitic ($C_{16}$) and stearic ($C_{18}$) acids and the unsaturated methyl esters of oleic ($C_{18}$ mono-unsaturated), linoleic ($C_{18}$ di-unsaturated), and α-linolenic ($C_{18}$ tri-unsaturated) acids. Preferred fatty alkyl esters derive from $C_6$-$C_{22}$ fatty acids or their mixtures, preferably $C_8$-$C_{18}$ fatty acids or their mixtures. In some instances, $C_{12}$-$C_{14}$ fatty acids may be preferred. Examples include methyl caprate, methyl myristate, methyl laurate, and methyl esters from coconut oil. Preferred fatty alkyl esters derive from $C_1$-$C_4$ alkanols, preferably methyl or ethyl esters, most preferably methyl esters.

Suitable amino acid salts are alkali metal and alkaline earth metal salts of amino acids. Preferred are alkali metal salts, particularly sodium and potassium salts, of amino acids selected from glycine, sarcosine, β-alanine, alanine, glutamic acid, and aspartic acid. Glycinates, sarcosinates, and glutamates are particularly preferred. Glycinates are most preferred.

Typically, an excess of the fatty alkyl ester is used. Preferably, the molar ratio of amino acid salt to fatty alkyl ester will be within the range of 50 to 110 mole %, more preferably from 80 to 100 mole %.

The reaction of the fatty alkyl ester and amino acid salt is preferably performed in the presence of an alkaline catalyst. Suitable alkaline catalysts include, for example, alkali metals as well as alkali metal and alkaline earth metal hydrides, hydroxides, alkoxides, carbonates, bicarbonates, carboxylates, and the like. Alkali metal alkoxides are preferred. When a fatty methyl ester is used, sodium methoxide or potassium methoxide is preferred. When an alkaline catalyst is used, it is preferred to use 0.1 to 20 mole %, more preferably 0.2 to 10 mole %, most preferably 1 to 5 mole %, of the catalyst relative to the amount of fatty alkyl ester.

The polyol is selected from glycerin and propylene glycol; mixtures of glycerin and propylene glycol can be used.

The polyol is used in an amount effective to keep the reaction mixture fluid. "Fluid" means that the reaction mixture maintains good flow properties at the reaction temperature; it remains stirrable and pumpable at reasonable energy demand. The skilled person can conveniently determine reaction mixture melting point (or conversely solidification point), together with molten reaction mixture viscosity, to judge whether a given outcome constitutes a fluid reaction mixture. When the polyol is omitted or used in too small a proportion, the reaction mixture can become extremely viscous or solidify, even at elevated temperature. In addition, the product can darken, conversion suffers, by-products (mostly di- and tripeptides) form, and excessive foaming can occur as volatiles (e.g., alkanols produced in the amidation reaction) become trapped in the viscous mixture. Examples 1 and 2 show the benefits of using enough glycerin, while Comparative Examples 3-5 illustrate the effect of using no glycerin or too little glycerin. As shown in Comparative Example 3, when no glycerin is used, conversion to the N-acyl amino acid salt is low, a high temperature is needed, and the reaction mixture solidifies upon partial conversion (40 mole %). Comparative Examples 4 and 5 show the impact on color, conversion, and foaming when inadequate glycerin is used. Examples 7 and 8 show that propylene glycol may achieve fluidity at lower usage levels.

The amount of polyol needed to maintain a fluid reaction mixture depends on the fatty ester chain length, the nature of the amino acid salt and polyol, the reaction temperature, and other factors. Preferably, however, at least 10 wt. %, more preferably at least 20 wt. %, of polyol is used based on the combined amounts of polyol, fatty alkyl ester, and amino acid salt.

Preferably, the polyol is used in an amount such that the melting point of the reaction mixture stays at least 10° C. below that of the reaction temperature at a conversion of amino acid salt to N-acyl amino acid salt greater than 70 mole %. More preferably, the polyol is used in an amount such that the melting point of the reaction mixture stays at least 20° C. below that of the reaction temperature at a conversion of amino acid salt to N-acyl amino acid salt greater than 70 mole %. The melting point of the reaction mixture normally increases as conversion proceeds toward completion. Thus, it is more challenging at high conversions to maintain a fluid reaction mixture and avoid the difficulties discussed above.

As the skilled person will appreciate, the reaction mixture melting point is influenced by the nature of the polyol and amino acid salt; the proportion of polyol; the chain length, branching, and distribution in the acyl group of the fatty ester; and other factors. Preferably, the reaction mixture maintains a melting point (i.e., a solidification temperature) less than 160° C., more preferably less than 150° C., most preferably less than 140° C.

Preferably, the reaction mixture will have a final viscosity less than 10,000 cP, more preferably less than 1000 cP, and most preferably less than 200 cP, where each viscosity is measured at the amidation reaction temperature.

In one specific example, when a mixture of at least about 70 to about 100 wt. % methyl laurate and about 0 to about 30 wt. % of methyl myristate is reacted with sodium glycinate in a reaction mixture comprising glycerin, it is preferred to use at least 30 wt. %, more preferably at least 35 wt. %, and most preferably at least 40 wt. %, of glycerin based on the combined amounts of glycerin, $C_{12}$-$C_{14}$ methyl esters, and glycinate salt.

In another specific example, when methyl laurate is reacted with sodium glycinate in a reaction mixture comprising propylene glycol, it is preferred to use at least 10 wt. %, more preferably at least 20 wt. %, and most preferably at least 25 wt. %, of propylene glycol based on the combined amounts of propylene glycol, methyl laurate, and glycinate salt.

Use of the polyol enables successful conversion to the desired N-acyl amino acid salt at relatively modest temperatures. Preferably, the amidation reaction of the fatty alkyl ester and amino acid salt is performed at a temperature within the range of 100° C. to 200° C., more preferably from 110° C. to 160° C., and most preferably from 120° C. to 150° C.

Conversion of the amino acid salt to the N-acyl amino acid salt is carried out to any desired degree. It may be desirable, for instance, to convert only a portion of the amino acid salt, thereby giving a mixture of the fatty alkyl ester and the amidation product. Preferably, however, at least 80 mole % of the amino acid salt is converted to the N-acyl amino acid salt. More preferably, at least 90 mole % of the amino acid salt is converted to the N-acyl amino acid salt.

The inventive process makes it possible to minimize the proportion of di- and triacylated by-products (also referred to herein as "di- and tripeptides") generated. Preferably, the amount of di- and triacylated by-products is less than 10 mole %, more preferably less than 5 mole %, based on the combined amounts of N-acyl amino acid salt and by-products.

Thus, when enough polyol is included, compatibility of the fatty alkyl ester and amino acid salt improves, thereby enabling low-temperature reactions and faster rates, and generating N-acyl amino acid salts having low color and a reduced proportion of di- and tripeptide by-products.

Preferably, water is substantially excluded from the amidation reaction, at least while conversion of the amino acid salt to the N-acyl amino acid salt is below 50 mole %. Water inhibits the amidation reaction and can produce elevated levels of soap. (As will be explained later, however, we surprisingly found that water addition can actually be beneficial when conversion is in the range of 50 to 90 mole %)

Reaction of the fatty alkyl ester and amino acid salt generates a $C_1$-$C_4$ alkanol, which is removed from the reaction mixture as it forms. When a fatty methyl ester is used, the alkanol is methanol. Progress of the amidation reaction is typically monitored by measuring the amount of alkanol collected and/or by using $^1$H NMR, titration, or other well-known techniques.

The desired product is an N-acyl amino acid salt. The salts have broad utility as anionic surfactants and are useful in such industries as personal care, laundry detergents, fabric treatment, industrial or household cleaners, emulsion polymerization, bleaching, and oilfield chemicals, among others. The N-acyl glycinates and N-acyl sarcosinates, particularly the alkali metal salts, are of particular interest in personal care applications such as body washes, shampoos, bar soaps, liquid hand soaps, and the like. The use of glycerin or propylene glycol as a fluidizing agent for the inventive process is particularly beneficial because many personal care products are formulated to include glycerin or propylene glycol. Consequently, there may be no need to remove the glycerin or propylene glycol from the N-acyl amino acid salt after it is prepared.

As noted earlier, the preparation of N-acyl amino acid salts is particularly challenging when the reactants are fatty methyl esters and alkali metal glycinates. This reaction is troublesome due to a lack of reagent compatibility, solidification of the reaction mixture at elevated process temperatures, color development, severe foaming during methanol removal, and significant by-product generation. These problems are evident from inspection of Comparative Example 3. This example shows that when the polyol (glycerin) is omitted, it is not possible to achieve even 50% conversion to the desired N-acyl glycinate salt without having the reaction mixture darken and solidify.

The inventive process addresses the particular need for an improved route to N-acyl glycinates when the starting material is a fatty methyl ester, particularly a $C_{10}$-$C_{14}$ fatty methyl ester. The unavailability, until now, of a highly economical process has likely hindered broad utilization of N-acyl glycinates, which are exceptionally mild anionic surfactants, in personal care and other applications.

Preparation of N-Acyl Amino Acid Salts from Polyol Esters

In another aspect, a polyol ester is used instead of or in addition to a fatty alkyl ester to prepare the N-acyl amino acid salt. "Polyol ester" as used herein means a mono-, di-, or triglyceride or a fatty mono- or diester of propylene glycol. Thus, the invention includes a process which comprises reacting a polyol ester selected from mono-, di- or triglycerides or fatty mono- or diesters of propylene glycol with an amino acid salt in the presence of added glycerin or propylene glycol to produce the N-acyl amino acid salt. The glycerin or propylene glycol is added in an amount effective to keep the reaction mixture fluid until conversion to the N-acyl amino acid salt reaches the desired level of completion. "Fluid" has the meaning given earlier.

In some instances, the polyol esters may be more readily available than the fatty alkyl esters. In fact, the fatty alkyl esters are frequently obtained by transesterifying polyol ester mixtures with lower alkanols. Moreover, the polyol ester may be, at least in some instances, better suited than the corresponding fatty alkyl ester for maintaining a fluid reaction mixture.

Typically, an excess of the polyol ester is used. Preferably, the molar ratio of amino acid salt to polyol ester will be within the range of 20 to 105 mole %, more preferably from 50 to 100 mole %.

Suitable amino acid salts have already been described. Optionally, the reaction of the polyol ester and the amino acid salt is performed in the presence of an alkaline catalyst. Suitable alkaline catalysts have already been described.

Preferably, the amidation reaction of the polyol ester and amino acid salt is performed at a temperature within the range of 100° C. to 200° C., more preferably from 110° C. to 160° C., and most preferably from 120° C. to 150° C.

At least some glycerin or propylene glycol is added to the reaction mixture, i.e., at least some glycerin or propylene glycol is not generated from amidation of a polyol ester. Preferably, at least 10 mole %, more preferably at least 20 mole %, and most preferably at least 35 mole %, of the glycerin or propylene glycol present in the reaction mixture at any given time was added to the reaction mixture as glycerin or propylene glycol. An advantage of using polyol esters is the ability to generate a portion of the glycerin or propylene glycol as the reaction proceeds, which helps to keep the reaction mixture fluid.

Suitable polyol esters are mono-, di- or triglycerides; fatty mono- or diesters of propylene glycol; or mixtures thereof. They can be produced, for instance, by reacting fatty acids, fatty acid halides, or fatty anhydrides with glycerin or propylene glycol using well-known methods. Many mono-, di-, and triglycerides are mixtures isolated from or prepared from natural sources, particularly natural oils such as coconut oil, olive oil, rapeseed oil, soybean oil, or the like. Thus, suitable polyol esters can be made by transesterifying a natural oil with glycerin to give a mixture of mono-, di-, and triglycerides or by transesterifying a natural oil with propylene glycol to give a mixture of fatty mono- and diesters of propylene glycol.

In one aspect, the polyol ester needed is generated in situ from a fatty alkyl ester. Thus, the fatty alkyl ester, glycerin, and the amino acid salt are heated, optionally in the presence of an alkaline catalyst. The fatty alkyl ester reacts at least in part with glycerin to give a mono- or diglyceride intermediate, which reacts with the amino acid salt to give the desired N-acyl amino acid salt. In this process, the N-acyl amino acid salt is generated in part from a polyol ester intermediate, with the remainder coming from a direct reaction of the fatty alkyl ester and amino acid salt. Thus, the esterification and amidation reactions can occur concurrently.

In another aspect, the polyol ester is generated from the fatty alkyl ester in a separate step, i.e., in the absence of the amino acid salt. This approach may facilitate removal of the alkanol formed by esterification. The resulting polyol ester can then be combined and reacted with the amino acid salt to give the N-acyl amino acid salt.

In yet another aspect, conversion of the polyol ester to the N-acyl amino acid salt is intentionally limited to less than full conversion, for example, by limiting the molar amount of amino acid salt used. Preferably, conversion of the acyl groups of the polyol ester to the N-acyl amino acid salt is 30 to 90 mole %, more preferably 40 to 85 mole %, most preferably 50 to 80 mole %. The resulting mixture comprises the N-acyl amino acid salt and a polyol ester, preferably a monoglyceride. Such mixtures may improve the performance of certain end-use formulations, e.g., personal cleansers. Limiting conversion of the acyl groups of the polyol ester to the N-acyl amino acid salt can keep the reaction mixture melting point low, reduce the need for added glycerin or propylene glycol, and allow a reduced reaction temperature to be used. Consequently, the resulting product can have low color and a low concentration of di- and tripeptide by-products.

Preparation of N-Acyl Amino Acid Salts in the Presence of Added Water

In other inventive processes, water is added to the reaction mixture when conversion of the amino acid salt to the N-acyl amino acid salt is in the range of 50 to 90 mole %. We surprisingly found that adding water significantly reduces color generation and by-product formation, particularly dipeptides. Moreover, we found unexpectedly that the amino acid salt continues to react with fatty esters after water addition such that more than 90% conversion to the desired N-acyl amino acid salt can be achieved while maintaining low color and only modest soap generation. The added water also helps to fluidize the reaction mixture and depress the reaction mixture melting point compared to its melting point in the absence of the added water.

Thus, one inventive process comprises reacting a fatty alkyl ester, a mono-, di- or triglyceride, or a fatty mono- or diester of propylene glycol with an amino acid salt in the presence of glycerin or propylene glycol to produce an N-acyl amino acid salt and optionally a $C_1$-$C_4$ alkanol. Any alkanol is removed from the reaction mixture as it forms. The glycerin or propylene glycol is used in an amount effective to keep the reaction mixture fluid until conversion to the N-acyl amino acid salt reaches the desired level of completion. Water is added to the reaction mixture when conversion of the amino acid salt to the N-acyl amino acid salt is in the range of 50 to 90 mole %, preferably from 60 to 85 mole %, most preferably from 70 to 80 mole %. If water is added when conversion is well below 50 mole %, too much of the ester is hydrolyzed to give soap rather than becoming amidated. On the other hand, if conversion exceeds 90 mole % before water is added, excessive color development cannot be avoided. Although soap is usually generated upon water addition, particularly when the polyol is glycerin, we surprisingly found that the level is modest (less than 15 mole %), and conversion of the amino acid salt to the N-acyl amino acid salt proceeds despite the added water.

The amount of water needed will depend on the nature of the fatty esters and amino acid salts, whether glycerin or propylene glycol is used, the reaction temperature, the desired product mixture, the desired actives level, the desired viscosity, and other factors. In some instances, it may be desirable to use a relatively large proportion of water, e.g., to reduce the actives level of the mixture. In other instances, it may be desirable to use only enough water to achieve color stabilization or a workable viscosity. Generally, however, it is preferred to use 1 to 300 wt. %, preferably 10 to 200 wt. %, more preferably 25 to 150 wt. %, and even more preferably 40 to 130 wt. % of water based on the total amount of charged reaction mixture.

Prior to any addition of water, the amidation reaction is preferably performed at a temperature within the range of 100° C. to 200° C., more preferably 110° C. to 160° C., and most preferably 120° C. to 150° C. After water addition, the amidation continues at a lower reaction temperature, preferably 80° C. to 160° C., more preferably 85° C. to 140° C.

Suitable amino acid salts, fatty alkyl esters, and polyol esters have already been described. The reaction is optionally performed in the presence of an alkaline catalyst. Suitable alkaline catalysts have already been described.

Examples 6-9 and Comparative Example 10 below (see Table 2) demonstrate the utility of adding water to the reaction mixture when conversion of sodium glycinate reaches at least 80 mole %. In each of Examples 6-9, generation of acyl glycinate continues (up to 91 mole %), soap generation is minimal (less than 13 mole %), color development is low, and polyglycinate generation is suppressed (less than 4 mole %).

The following examples merely illustrate the invention. Those skilled in the art will recognize many variations that are within the spirit of the invention and scope of the claims.

EXAMPLE 1

Preparation of an N-Acyl Glycinate

This example demonstrates the utility of using enough glycerin to enable the preparation of sodium acyl glycinate from a $C_{12}$-$C_{14}$ methyl ester and sodium glycinate.

A reaction flask fitted with mechanical stirrer, Dean-Stark trap, overhead condenser, and nitrogen inlet is charged with a 72:26 mixture of methyl laurate and methyl myristate (33.3 g, 0.15 mol), sodium glycinate (15 g, 0.15 mol), glycerin (48.3 g, 0.52 mol), and sodium methoxide (0.28 g of 30 wt. % solution in methanol, 0.0015 mol). After heating for 2 h at 135° C., about 5 mL of MeOH is collected. When conversion of sodium glycinate to the N-acyl glycinate reaches 90+ mol % (confirmed by $^1$H NMR and titration), the molten product is cooled to room temperature. Water (65 g) is added with constant shaking to give an aqueous solution.

EXAMPLE 2

Preparation of an N-Acyl Glycinate

The procedure of Example 1 is generally followed with a reduced level of glycerin as indicated in Table 1. Reaction time is extended to 3 h. The reaction mixture remains molten and fluid at the reaction temperature (140° C.). The mixture is cooled to room temperature without further treatment. Conversion is high (99 mol %), although the Gardner color (13), fatty acid yield (17 mol %), or diglycinate yield (9.5 mol %) may be higher than desirable for some end-use applications.

COMPARATIVE EXAMPLE 3

Effect of No Glycerin

The procedure of Example 1 is generally followed except that no glycerin is used. After heating for 1 h at 145-165° C., the reaction mixture becomes dark pink and solidifies. The mixture is cooled to room temperature without further treatment. Conversion of sodium glycinate to N-acyl glycinate is 40 mol %.

COMPARATIVE EXAMPLE 4

Effect of Low Glycerin

The procedure of Example 1 is generally followed except that 14.5 g (0.16 mol) of glycerin is used. After heating for 80 min. at 145-155° C., the reaction mixture becomes dark pink and solidifies. The mixture is cooled to room temperature without further treatment. Conversion of sodium glycinate to N-acyl glycinate is 68 mol %.

COMPARATIVE EXAMPLE 5

Effect of Low Glycerin

The procedure of Example 1 is generally followed except that 24.2 g (0.26 mol) of glycerin in used. After heating for 3 h at 145-150° C., the reaction mixture does not solidify, but foaming is severe. The mixture is cooled to room temperature without further treatment. Conversion of sodium glycinate to N-acyl glycinate is 80 mol %.

Table 1 summarizes results from Examples 1 and 2 and Comparative Examples 3-5. As the skilled person will recognize, the values for the fatty acid and diglycinate in Comparative Examples 3 and 4 are relatively low because the reaction mixture foamed and solidified, forcing an early termination of the reaction.

TABLE 1

Preparation of N-Acyl Glycinates

| Example | 1 | 2 | C3 | C4 | C5 |
|---|---|---|---|---|---|
| polyol | glycerin | glycerin | none | glycerin | glycerin |
| mass ratio of polyol to methyl ester and sodium glycinate (w/w) | 1.0 | 0.70 | 0 | 0.25 | 0.50 |
| reaction temp (° C.) | 135 | 140 | 145-165 | 145-155 | 145-150 |
| reaction time (min) | 120 | 180 | 60[b] | 80[b] | 180 |
| product mp (° C.) | 105 | 125 | | | 145 |
| Gardner color[a] | 4.0 | 13 | — | 8.0 | 8.8 |
| severe foaming? | no | no | N/A | N/A | yes |
| mixture solidified at the reaction temperature? | no | no | yes | yes | no |
| conversion of sodium glycinate (mol %) | 95 | 99 | 40 | 68 | 80 |
| fatty acid yield (mol %) | 11 | 17 | 14 | 12 | 32 |
| monoglycinate yield (mol %) | 74 | 68 | 39 | 68 | 63 |
| diglycinate yield (mol %) | 6.7 | 9.5 | 1.8 | 1.8 | 8.3 |

N/A = not applicable
[a]20 wt. % reaction products dissolved in water, Lovibond ® PFX995 tintometer (from The Tintometer Ltd., Salisbury, UK), 10-mm cell path.
[b]Reaction terminated early because reaction mixture solidified.

EXAMPLES 6-9 and COMPARATIVE EXAMPLE 10

Water Addition to Molten Reaction Mixture

EXAMPLE 6

Preparation of an N-Acyl Glycinate

The procedure of Example 1 is generally followed. After heating for 2 h at 135° C., about 5 mL of MeOH is collected. When conversion of sodium glycinate to N-acyl glycinate reaches 80 mol %, the mixture is cooled to 125° C., i.e., about 10° C. above the melting point of the mixture. Water (65 g) is added to the molten mixture to continue the reaction. The mixture is heated at 90° C. for 30 min., then cooled to room temperature. Conversion of sodium glycinate to N-acyl glycinate in the molten stage (i.e., prior to any water addition) is 85 mol %. In the final aqueous product, conversion of sodium glycinate to the N-acyl glycinate is 91 mol %.

EXAMPLE 7

Preparation of an N-Acyl Glycinate

The procedure of Example 1 is generally followed except that propylene glycol (24.2 g, 0.32 mol) is used instead of glycerin. After heating for 2 h at 135° C., the reaction mixture remains fluid. Water is added to continue the reaction. Conversion of sodium glycinate to N-acyl glycinate at the molten stage is 88 mol %. In the final aqueous product, conversion of sodium glycinate to the N-acyl glycinate is 91 mol %.

EXAMPLE 8

Preparation of an N-Acyl Glycinate

The procedure of Example 7 is generally followed except that 14.5 g (0.19 mol) of propylene glycol is used. After heating for 3 h at 145° C., the reaction mixture remains fluid. Water is added to continue the reaction. Conversion of sodium glycinate to N-acyl glycinate at the molten stage is 80 mol %. In the final aqueous product, conversion of sodium glycinate to the N-acyl glycinate is 83 mol %.

EXAMPLE 9

Preparation of an N-Acyl Glycinate

The procedure of Example 1 is generally followed except that a mixture of glycerin (19.4 g, 0.21 mol) and propylene glycol (4.8 g, 0.063 mol) is used. After heating for 2.5 h at 145-150° C., the reaction mixture remains fluid, although mild foaming is observed. Water is added to continue the reaction. Conversion of sodium glycinate to N-acyl glycinate at the molten stage is 85 mol %. In the final aqueous product, conversion of sodium glycinate to the N-acyl glycinate is 88 mol %.

COMPARATIVE EXAMPLE 10

No Water Addition

The procedure of Example 6 is generally followed, except that slightly more glycerin is used and the reaction time is extended to 3.3 h. The mixture is cooled to room temperature without further treatment. Results appear in Table 2.

Examples 6-9 demonstrate the utility of adding water to the reaction mixture when conversion of sodium glycinate reaches at least 80 mol %. In each case, generation of acyl glycinate continues, soap generation is minimal, color development is low, and polyglycinate generation is suppressed. Although the longer reaction time in Comparative Example 10 gives >90 mole % conversion (like Example 6), the absence of water addition results in more color development (Gardner color=11 versus 4.2) and higher levels of fatty acid (17 mol % versus 12 mol %) and diglycinates (5.8 mol % versus 3.6 mol %) when compared with Example 6. Table 2 summarizes the results.

TABLE 2

Preparation of N-Acyl Glycinates with Water Addition

| | Before Water Addition | | | | | After Water Addition | | | |
|---|---|---|---|---|---|---|---|---|---|
| | Example | | | | | | | | |
| | 6 | 7 | 8 | 9 | C10 | 6 | 7 | 8 | 9 |
| polyol | glycerin | PG | PG | glycerin + PG | glycerin | | | | |
| mass ratio of polyol to methyl ester and sodium glycinate | 0.7 | 0.5 | 0.3 | 0.5 | 0.75 | | | | |
| reaction temp (° C.) | 135 | 135 | 145 | 145-150 | 135 | 90 | 90 | 90 | 90 |
| reaction time (min) | 120 | 120 | 180 | 150 | 200 | 30 | 30 | 30 | 30 |
| product mp (° C.) | 125 | 116 | 120 | 120 | 125 | | | | |
| Gardner color[a] | | | | | 11 | 4.2 | 4.0 | 3.7 | 4.0 |
| conversion of sodium glycinate (mol %) | 85 | 88 | 80 | 85 | 91 | 91 | 91 | 83 | 88 |
| fatty acid yield (mol %) | 5.6 | 9.6 | 4.5 | 9.9 | 17 | 12 | 8.8 | 4.9 | 13 |
| monoglycinate yield (mol %) | 73 | 74 | 69 | 68 | 71 | 75 | 81 | 71 | 71 |
| diglycinate yield (mol %) | 2.7 | 2.0 | 1.9 | 2.5 | 5.8 | 3.6 | 1.9 | 1.8 | 3.5 |

PG = propylene glycol
[a]20 wt. % reaction products dissolved in water, Lovibond ® PFX995 tintometer (from The Tintometer Ltd., Salisbury, UK), 10-mm cell path.

COMPARATIVE EXAMPLE 11

Effect of Added Isobutanol

The procedure of Example 1 is generally followed except that a mixture of glycerin (19.4 g, 0.21 mol) and isobutanol (4.8 g, 0.065 mol) is used. After heating for 3 h at 145° C., the reaction mixture (although fluid) exhibits mild foaming, and the reaction mixture melting point approaches the reaction temperature. The mixture is cooled to room temperature without further treatment. Conversion of sodium glycinate to N-acyl glycinate at the molten stage is 67 mol %.

This example illustrates a traditional solvent approach to making an N-acyl glycinate. Conversion is somewhat lower than desirable at the practical endpoint of the reaction, and the isobutanol would normally need to be removed from the product.

EXAMPLE 12

Monoglyceride Intermediate

A reaction flask fitted with mechanical stirrer, Dean-Stark trap, overhead condenser, and nitrogen inlet is charged with a 72:26 mixture of methyl laurate and methyl myristate (33.3 g, 0.15 mol), glycerin (37.5 g, 0.41 mol), and sodium methoxide (0.28 g of 30% solution in methanol, 0.0015 mol). After heating for 3 h at 125° C., about 5 mL of MeOH is collected and $^1$H NMR analysis confirms that the reaction mixture comprises monoglycerides. Sodium glycinate (15 g, 0.15 mol) is added in one portion. When conversion of sodium glycinate to the N-acyl glycinate reaches 90 mol %, the molten product is cooled to room temperature. Water (65 g) is added with good mixing to give an aqueous solution.

This example illustrates generation of a monoglyceride from a mixture of fatty methyl esters in a first step (i.e., in the absence of the amino acid salt). The monoglyceride is converted smoothly to the desired N-acyl glycinate upon addition of the amino acid salt.

EXAMPLE 13

Preparation of an N-Acyl Sarcosinate

The procedure of Example 1 is followed except that sodium sarcosinate (16.6 g, 0.15 mol) is used instead of sodium glycinate. When conversion of sodium sarcosinate to the N-acyl sarcosinate reaches 90 mol %, the molten product is cooled to room temperature. Water (65 g) is added with good mixing to give an aqueous solution.

EXAMPLE 14

Monoglyceride Intermediate

The procedure of Example 12 is generally followed except that sodium sarcosinate (16.6 g, 0.15 mol) is used instead of sodium glycinate. When conversion of sodium sarcosinate to the N-acyl sarcosinate reaches 90 mol %, the molten product is cooled to room temperature. Water (65 g) is added with good mixing to give an aqueous solution.

As shown in Examples 13 and 14, the inventive processes can be used to prepare N-acyl sarcosinates or other N-acyl amino acid salts that are traditionally easier to prepare than N-acyl glycinates.

The preceding examples are meant only as illustrations. The following claims define the invention.

We claim:

1. A process which comprises reacting a fatty alkyl ester with an amino acid salt in the presence of a polyol selected from the group consisting of glycerin and propylene glycol to produce an N-acyl amino acid salt and a $C_1$-$C_4$ alkanol, wherein the alkanol is removed from the reaction mixture as it forms, and wherein the polyol is used in an amount effective to keep the reaction mixture fluid until conversion to the N-acyl amino acid salt reaches the desired level of completion.

2. The process of claim 1 wherein the fatty alkyl ester is a $C_6$-$C_{22}$ methyl ester.

3. The process of claim 1 wherein the amino acid salt is an alkali metal salt of an amino acid selected from the group consisting of glycine, sarcosine, β-alanine, alanine, glutamic acid, and aspartic acid.

4. The process of claim 1 wherein the amino acid salt is an alkali metal salt of glycine.

5. The process of claim 1 wherein the reaction is performed in the presence of an alkaline catalyst.

6. The process of claim 5 wherein 0.2 to 10 mole % of the alkaline catalyst is used.

7. The process of claim 1 wherein the polyol is glycerin.

8. The process of claim 1 wherein the reaction is performed at a temperature within the range of 100° C. to 200° C.

9. The process of claim 1 wherein at least 20 wt. % of polyol is used based on the combined amounts of polyol, fatty alkyl ester, and amino acid salt.

10. The process of claim 1 wherein the polyol is used in an amount effective to keep the melting point of the reaction mixture at least 10° C. below that of the reaction temperature at a conversion of amino acid salt to N-acyl amino acid salt greater than 70 mole %.

11. The process of claim 1 wherein water is added to the reaction mixture when conversion of the amino acid salt to the N-acyl amino acid salt is in the range of 50 to 90 mole %.

12. The process of claim 1 wherein conversion of the amino acid salt to the N-acyl amino acid salt is at least 90 mole %.

13. The process of claim 1 wherein the reaction mixture has a final viscosity less than 10,000 cP at the reaction temperature.

14. A process which comprises reacting a polyol ester selected from mono-, di- or triglycerides or fatty mono- or diesters of propylene glycol with an amino acid salt in the presence of an added polyol selected from the group consisting of glycerin and propylene glycol to produce an N-acyl amino acid salt, wherein the polyol is added in an amount effective to keep the reaction mixture fluid until conversion to the N-acyl amino acid salt reaches the desired level of completion.

15. The process of claim 14 wherein the triglyceride is isolated or prepared from a natural oil.

16. The process of claim 14 wherein the amino acid salt is an alkali metal salt of an amino acid selected from the group consisting of glycine, sarcosine, β-alanine, alanine, glutamic acid, and aspartic acid.

17. The process of claim 14 wherein the amino acid salt is an alkali metal salt of glycine.

18. The process of claim 14 wherein the reaction is performed in the presence of an alkaline catalyst.

19. The process of claim 14 wherein the reaction is performed at a temperature within the range of 100° C. to 200° C.

20. The process of claim 14 wherein the polyol is used in an amount effective to keep the melting point of the reaction mixture at least 10° C. below that of the reaction temperature at a conversion of amino acid salt to N-acyl amino acid salt greater than 70 mole %.

21. The process of claim 14 wherein the reaction is performed in the presence of a fatty alkyl ester.

22. The process of claim 14 wherein the reaction product comprises a mixture of the N-acyl amino acid salt and at least one monoglyceride.

23. The process of claim 14 wherein water is added to the reaction mixture when conversion of the amino acid salt to the N-acyl amino acid salt is in the range of 50 to 90 mole %.

24. The process of claim 15 wherein conversion of acyl groups of the polyol ester to the N-acyl amino acid salt is within the range of 30 mole % to 90 mole %.

25. The process of claim 14 wherein the reaction mixture has a final viscosity less than 10,000 cP at the reaction temperature.

26. A process which comprises reacting a fatty alkyl ester, a mono-, di- or triglyceride, or a fatty mono- or diester of propylene glycol with an amino acid salt in the presence of a polyol selected from the group consisting of glycerin and propylene glycol to produce an N-acyl amino acid salt and optionally a $C_1$-$C_4$ alkanol, wherein any alkanol is removed from the reaction mixture as it forms, the polyol is used in an amount effective to keep the reaction mixture fluid until conversion to the N-acyl amino acid salt reaches the desired level of completion, and water is added to the reaction mixture when conversion of the amino acid salt to the N-acyl amino acid salt is in the range of 50 to 90 mole %.

\* \* \* \* \*